United States Patent
Bourg, Jr. et al.

(10) Patent No.: US 8,887,546 B2
(45) Date of Patent: Nov. 18, 2014

(54) METHOD FOR DECREASING VARIABILITY IN A MOISTURE ANALYZER

(71) Applicant: Frito-Lay North America, Inc., Plano, TX (US)

(72) Inventors: Wilfred M. Bourg, Jr., Melissa, TX (US); Scott Fagan, Dallas, TX (US)

(73) Assignee: Frito-Lay North America, Inc., Plano, TX (US)

( * ) Notice: Subject to any disclaimer, the term of this patent is extended or adjusted under 35 U.S.C. 154(b) by 0 days.

(21) Appl. No.: 13/783,591

(22) Filed: Mar. 4, 2013

(65) Prior Publication Data

US 2013/0174634 A1 Jul. 11, 2013

Related U.S. Application Data

(62) Division of application No. 12/873,907, filed on Sep. 1, 2010, now Pat. No. 8,408,051.

(51) Int. Cl.
| | |
|---|---|
| *G01N 3/62* | (2006.01) |
| *G12B 13/00* | (2006.01) |
| *G01N 5/02* | (2006.01) |
| *G01N 33/00* | (2006.01) |
| *G01N 15/02* | (2006.01) |
| *G01N 25/00* | (2006.01) |

(52) U.S. Cl.
CPC ............ *G01N 33/00* (2013.01); *G01N 15/0205* (2013.01); *G01N 25/00* (2013.01)
USPC ................................................ 73/1.01; 73/73

(58) Field of Classification Search
CPC .......... G01N 25/00; G01N 33/00; A23L 1/217
USPC ....................................................... 73/1.01, 73
See application file for complete search history.

(56) References Cited

U.S. PATENT DOCUMENTS

| | | | | |
|---|---|---|---|---|
| 4,277,510 | A | * | 7/1981 | Wicklund et al. .............. 426/441 |
| 5,448,904 | A | * | 9/1995 | Zuckerwar et al. ............. 73/1.82 |
| 5,949,678 | A | * | 9/1999 | Wold et al. ........................ 700/83 |
| 5,983,711 | A | * | 11/1999 | Pappas et al. ...................... 73/76 |
| 6,257,956 | B1 | * | 7/2001 | Shteinhauz et al. .............. 451/8 |
| 6,584,836 | B1 | * | 7/2003 | Shteinhauz et al. ............ 73/146 |
| 6,991,121 | B1 | * | 1/2006 | Kipperman et al. ......... 215/11.1 |
| 7,487,662 | B2 | * | 2/2009 | Schabron et al. .............. 73/23.2 |
| 8,036,838 | B2 | * | 10/2011 | Parkinson ........................ 702/55 |
| 2006/0108545 | A1 | * | 5/2006 | Yoshiki et al. ........... 250/492.21 |
| 2007/0141227 | A1 | * | 6/2007 | Boudreaux et al. ........... 426/637 |
| 2008/0138480 | A1 | * | 6/2008 | Bows et al. .................... 426/465 |
| 2008/0190173 | A1 | * | 8/2008 | Wienand et al. ............. 73/28.01 |

* cited by examiner

*Primary Examiner* — Hezron E Williams
*Assistant Examiner* — David Z Huang
(74) *Attorney, Agent, or Firm* — Colin P. Cahoon; Celina M. Orr; Carstens & Cahoon, LLP

(57) ABSTRACT

A method for analyzing moisture content in an analyzer. In one embodiment a sample is introduced into an analyzer and an initial weight is obtained. The sample is then fortified where it is allowed to pick-up moisture. The temperature of the analyzer is increased and an initial fortified point is obtained wherein the sample has returned to its initial weight. Thereafter the analyzer obtains the final moisture content of the sample at a test finish time. In one embodiment satellite analyzers are biased against a standard analyzer so that more uniform results are obtained.

19 Claims, 7 Drawing Sheets

METHOD FOR DECREASING VARIABILITY IN A MOISTURE ANALYZER

CROSS REFERENCE TO RELATED APPLICATION

This application is a divisional application of co-pending U.S. patent application Ser. No. 12/873,907, entitled "Method for Decreasing Variability in a Moisture Analyzer," filed Sep. 1, 2010, the technical disclosure of which is hereby incorporated by reference in its entirety.

BACKGROUND OF THE INVENTION

1. Technical Field

The present invention relates to a method for use in an analytical furnace.

2. Description of Related Art

Analyzers can be used to measure or calculate a product's weight, moisture, volatiles, fixed carbon, ash, etc. of a sample. Often an analyzer utilizes a furnace or other heat source to heat a sample. One type of analyzer is a thermogravimetric analyzer which periodically weighs the sample. The analyzer utilizes ASTM standards to analyze the sample and provide the desired reading. The sample is first initially weighed. Thereafter it is subjected to a controlled temperature profile where it is periodically weighed to determine weight loss. The moisture content can be calculated based on the measured weight loss.

The temperature of the sample within the analyzer is measured and controlled using a temperature sensor such as a thermocouple. Often thermocouples and other temperature measuring devices drift and become inaccurate over time. As the thermocouples become inaccurate, the control scheme which controls the temperature of the sample often subjects the sample to non-uniform temperature ramp-up which affects the amount and rate of moisture loss from the sample. As such, the temperature profile is not accurately known or controlled, which can result in increased error and variability. Accordingly, it is desirable to have a method which accounts for and overcomes this inaccuracy.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Several embodiments of Applicant's invention will now be described with reference to the drawings. Unless otherwise noted, like elements will be identified by identical numbers throughout all figures. The invention illustratively disclosed herein suitably may be practiced in the absence of any element which is not specifically disclosed herein.

Figure 1:
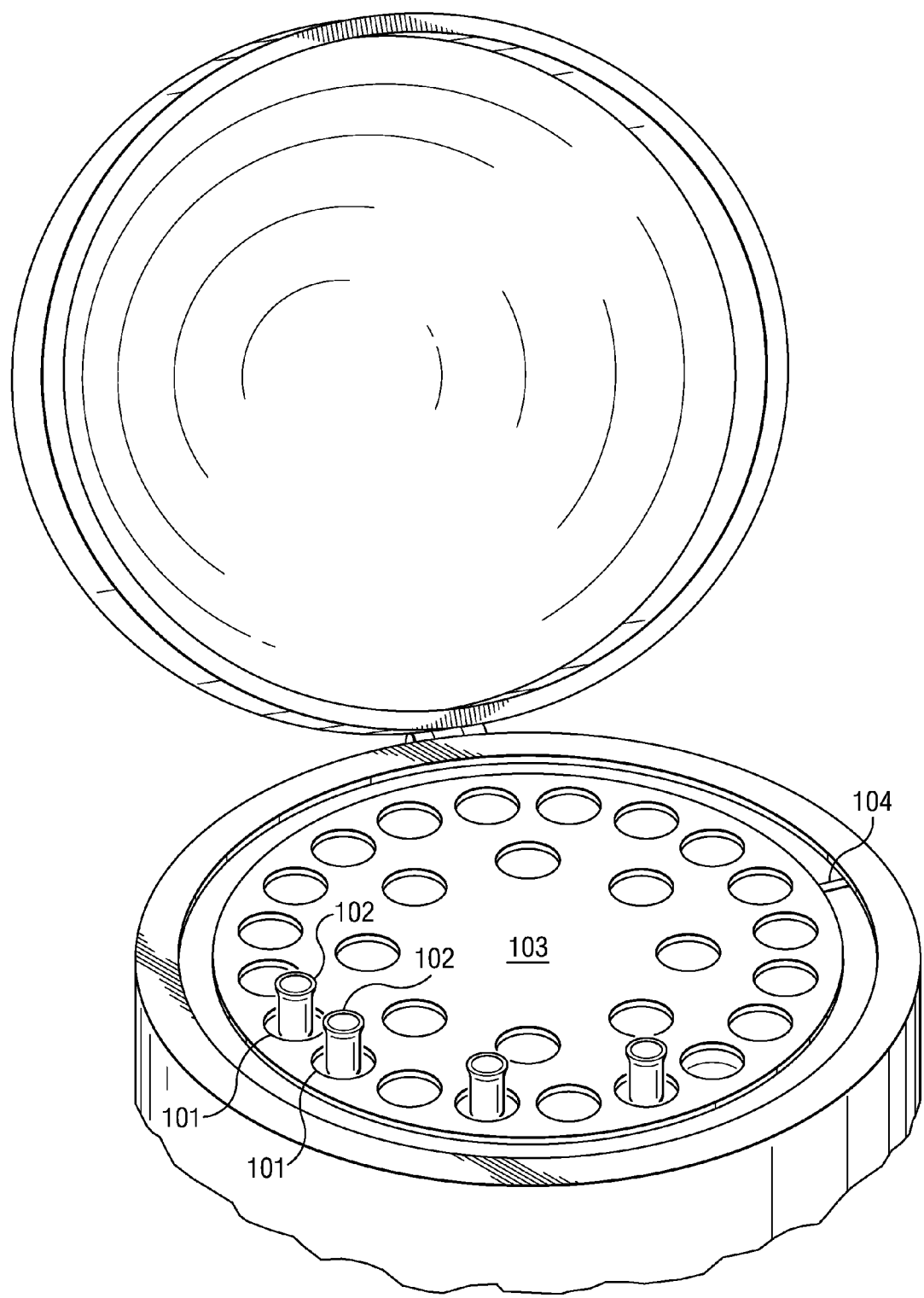
FIG. 1 is perspective view of an analyzer in one embodiment.

FIG. 1 refers to an analyzer in one embodiment. As used herein an analyzer refers to a device which can determine the moisture content of a sample. The analyzer may also have additional capabilities. In one embodiment the analyzer accurately weighs a sample as it is being heated to determine the moisture lost over time. In one embodiment the analyzer comprises a forced air oven. Virtually any dehydration oven that can measure weight loss over time can be utilized. In one embodiment the analyzer comprises a thermogravimetric analyzer. As depicted, the analyzer comprises a plurality of apertures 101. In one embodiment the analyzer comprises only a single aperture 101 whereas in other embodiments the analyzer comprises more than one aperture 101. In one embodiment the analyzer comprises ten or more apertures 101. In one embodiment the apertures 101 are located on a plate 103, and in one embodiment the apertures are evenly spread across the circumference of the plate 103. Sitting within each aperture is a crucible 102. The crucible 102 is used to contain the sample. The crucible 102 can be made of any material which can tolerate elevated temperatures and which will not react with the sample. In one embodiment the crucible 102 comprises a ceramic material.

The sample can comprise virtually any material. In one embodiment the sample comprises food stuffs such as dough, baked product, fried product, or extruded product. The sample can also comprise polymers, plastics, paper, wood, coal, or any product that has its moisture content determined. In one embodiment the material comprises a low moisture product. In one embodiment the material comprises an initial moisture content of less than about 30%. In another embodiment the material comprises an initial moisture content of less than about 10%. In still another embodiment the material comprises an initial moisture content of less than about 5%. In one embodiment the material is hygroscopic and cannot be aggressively dehydrated at high temperatures because components other than water will volatize or flash off.

In one embodiment the analyzer comprises a heating element. The heating element can comprise any device used to supply heat, including but not limited to, electric heat or heat through combustion. Virtually any type of heat that can dehydrate a product can be used. The temperature within the analyzer is measured by at least one temperature sensor 104. The temperature sensor 104 can be located at virtually any location within the analyzer. In one embodiment the temperature sensor 104 is located at a location below the plate 103. The temperature sensor 104 can comprise a thermocouple or other suitable temperature sensor. In one embodiment the temperature sensors 104 are coupled to a control system. The temperature sensor 104 provides a signal to the control system to indicate the temperature within the analyzer. The control system can comprise any control system known to control a system or process. In one embodiment the control system adjusts process variables to obtain a desired set point. A process variable is any variable which can be adjusted and includes temperature, humidity, pressure, etc. It should be understood, that as used herein "obtain" refers to obtaining or reaching a set-point within an acceptable margin of error. If the acceptable margin of error is 20%, then if the measured moisture content is within 20% of the set point moisture content then the moisture content set-point has been obtained.

In one embodiment the temperature sensor 104 is used to obtain a set-point temperature. A set-point temperature is the temperature that the analyzer seeks to obtain. In one embodiment, the set-point temperature is obtained by comparing the measured temperature relayed from at least one of the temperature sensors 104 to the desired set-point temperature. A control system then adjusts the process variables as necessary to obtain the desired set-point temperature. In one embodiment the control system adjusts the heating element.

The analyzer further comprises at least one balance. A "balance" as used herein refers to any device which determines the weight of a sample. In one embodiment the analyzer comprises a single balance and each crucible 102 is sequentially rotated and weighed with the balance. In one embodiment the crucibles 102 are first tared prior to introducing the sample into the analyzer. In one embodiment the plate 103 rotates until the sample desired to be weighed is above the balance. The plate 103 then lowers so that the desired crucible 102 is supported by the balance and its weight is determined. Thereafter the plate 103 raises, rotates, and weighs the next crucible 102 in line. In this manner the initial weight of each sample is obtained. In one embodiment comprising nineteen crucibles 102, each sample is weighed approximately every four minutes. In such an embodiment the weight of the sample is recorded and obtained every four minutes. Thus, the moisture gain or loss can be measured against time. In other embodiments the number of crucibles 102, as well as the rotation time, will be adjusted. For example, one embodiment comprises fifteen crucibles which are weighed every three minutes.

In operation, the crucible 102 in the first position is first filled with a sample and weighed to obtain an initial weight. Thereafter, a crucible 102 next in succession is filled and weighed. In the prior art operation, the analyzer is then ramped to a set-point temperature. As the sample is heated its moisture content decreases as it loses moisture. The set-point temperature is chosen to obtain a desired final moisture content. In operation, the set-point temperature utilized to yield the desired final moisture content varies wildly across different analyzers.

The amount of heat supplied to the samples (Q) can be defined as follows, $$Q_{heat\ transfer\ to\ sample} = U * \text{Area} * (T_{System\ Set\ Point} - T_{boiling})$$

Where $T_{System\ Set\ Point}$: Is the set-point temperature
$T_{boiling}$: Is the boiling temperature of water
U*Area: Is the heat transfer co-efficient and the area The boiling temperature will be fairly constant in a single location but can change at different locations due to elevation changes and other factors such as weather conditions. The U*Area segment of the equation should remain relatively constant between systems but may change slightly due to system degradation, etc. However, the set-point temperatures often vary across systems. This can due in part to thermocouple drift as discussed previously. Even the same model of analyzers which operate within the same room can require varied set-point temperatures to achieve a desired moisture. In the prior art operation, if a specific moisture is not reached then the set-point temperature is adjusted accordingly. The set-point temperature can drift for a variety of reasons including thermocouple drift whereby the thermocouple gradually becomes less accurate. Such drift can cause the set-point temperature to vary from the actual operating temperature causing inconsistencies.

In one embodiment, Applicant has discovered that to make the amount of heat supplied to a sample uniform across various analyzers the dehydration driving force, which is the difference between the temperature within the analyzer and the boiling point temperature, should be held constant. As discussed above the U*Area portion of the equation is relatively constant across analyzers of the same type. Thus, by making the dehydration driving force uniform, the test can become more accurate. As will be discussed below, the set-point temperature for each analyzer will be adjusted to ensure the dehydration driving force remains approximately constant.

Figure 2:
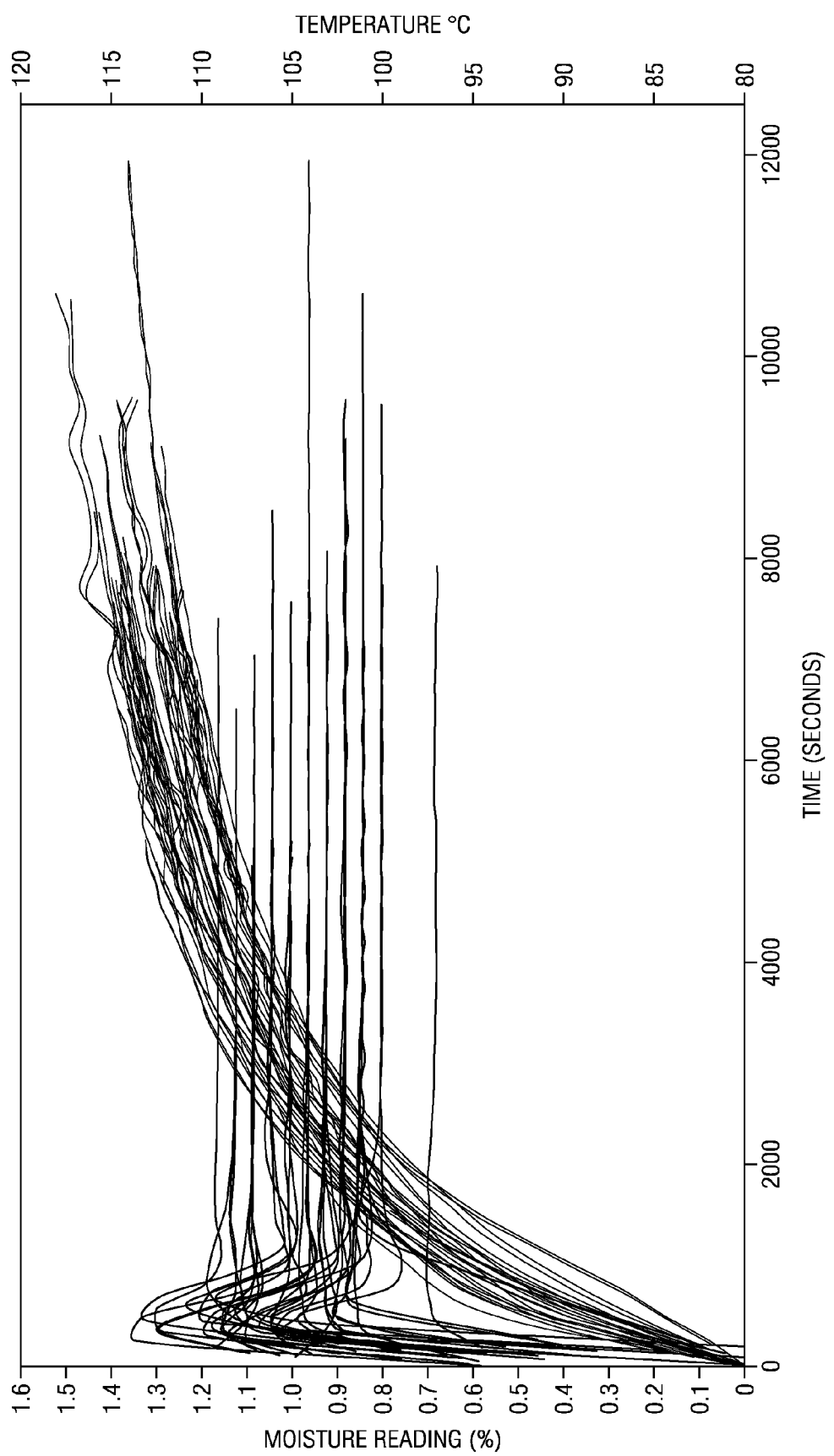
FIG. 2 is a temperature and moisture profile from a plurality of analyzers.

FIG. 2 illustrates the temperature and moisture content profiles of a number of analyzers in different locations across the country. Each profile represents a reference product performed on 39 different analyzers located at various places in the United States. All of the reference product was prepared at the same time, at the same location, and were packed into centrifuge tubes to prevent moisture pickup prior to analyzing each sample at the different analyzers. The analyzers utilized were a TGA 701 thermogravimetric analyzer made by Leco Corporation of St. Joseph Michigan. Each analyzer analyzed two reference samples in a single batch. As depicted, the reference product comprised potato dough.

As noted, the analyzers are analyzing reference samples which have an approximately equal starting moisture content. The left axis shows the weight of the sample that has been lost or gained over time expressed in percent moisture. A positive moisture reading indicates that moisture has been lost whereas a negative reading indicates that moisture has been gained. It can be seen that the final moisture reading ranges from about 1.5% to about 1.2%. Accordingly, this resulted in a range of approximately 0.3% moisture. This means that the same sample yielded various results on different analyzers. Because the moisture reading obtained from the analyzer is often used to control processing conditions for making a final product, the variance across analyzers can result in significant product variability. Reducing the variance of the moisture content obtained by the analyzer will result in decreased product variability. Further, as will be discussed in detail below, the moisture content has an affect on many final product attributes including staleness, number of defects, level of scorching, acrylamide formation, product hardness, etc. These and other attributes can be better controlled by better controlling the moisture content.

FIG. 2 also illustrates the temperature profile of the sample. As can be seen, each analyzer seeks to obtain the set-point temperature. As the temperature profile becomes horizontal, the temperature set-point has been obtained. As can be seen, the temperature set-point varies from about 109° C. to about 97° C. across different analyzers. This illustrates the inaccuracy of the temperature sensors. As an example, one of the analyzers has a set point temperature of about 97° C. which is less than the boiling temperature of water. Because water is being evaporated from the sample, it is clear that the analyzer is operating above 100° C. Accordingly, the temperature reported by the sensor is incorrect. As discussed, each of these varying set-point temperatures is chosen to achieve a set-point moisture content. In the case of the analyzer with a set-point temperature of 97° C. it is possible that this temperature sensor trended downward so that a progressively lower and lower set-point temperature was required to achieve the desired moisture content. The actual set-point temperature may be 105° C. but is being read as 97° C.

FIG. 2 also illustrates the temperature profile before the set-point temperature is obtained. It can be seen that some of the analyzers overshoot the set-point temperature. This can be due in part to different control systems used to control the temperature as well as errors in the temperature sensor. Thus the sample is being subjected to temperatures which can be much greater than the set-point temperature. Because water vapor is a function of temperature, the ramp profile has an affect on the water vapor of the sample. This affects the measured moisture content. As can be seen from the figure, the analyzers have different ramp profiles. A ramp profile is the temperature profile while the set-point temperature is being obtained.

Aside from the differences already discussed, it can be seen that the total testing time differs from each test as well. The total testing time refers to the total length in time from when the sample is first loaded until the test is complete. In one embodiment the test is complete when the rate of change in the moisture content reached a specified value. It can be seen that there is great variability in the total testing time which is undesirable as it increases variability of the product and product control.

The previous methods of measuring moisture content are inadequate for a variety of reasons. First, it often takes time to load all the samples. During this waiting time, the moisture content of the sample is likely to change due to the sample taking in or losing moisture to the air. As those skilled in the art will understand, the change in moisture content will depend on a plurality of factors including sample moisture content, temperature of the sample, temperature of the air, humidity of the air, etc. Further, the material may have components which can either oxidize or volatilize which also changes the weight of the sample, which in turn changes the moisture content. As can be appreciated, the first loaded sample may change more than the last loaded sample as the first loaded sample is often exposed to air for a greater period of time than the last loaded sample. This introduces non-uniformity into the system.

Second, as discussed, the ramp profile is not uniform across the various analyzers. Because water vapor is a function of temperature, the slope of the ramp profile affects the water vapor of the sample. This alters the amount and speed of moisture loss which introduces further non-uniformity into the system.

Third, as discussed, the total testing time is not uniform across the various analyzers. This results in some samples being analyzed for a much longer time than other samples which can introduce non-uniformity into the system. Applicants have discovered several methods, discussed herein, which can overcome and eliminate the non-uniformity of the ramp profiles and the total testing times. Further, as discussed above, often the first loaded samples have increased exposure to air compared to later loaded samples. Applicants can overcome this and other moisture variances in the samples caused by exposure to air by the methods discussed herein. Finally, by employing the methods discussed herein, Applicants eliminate the non-uniformity by overcoming or accounting for the issues previously addressed such as incorrect temperature sensors resulting in set point temperature variances.

In one embodiment the samples are thermally fortified during the ramp-up profile. In one embodiment, the thermal fortification comprises allowing the sample to pick-up moisture before heat is applied to remove moisture. Picking-up moisture refers to increasing the moisture content of the sample. This can be accomplished by opening the lid of the analyzer so that the samples are subject to the air, for example. The air can be modified such as by using a humidifier to obtain a desired humidity. Those skilled in the art will understand that the humidity of the air can be adjusted to control the rate of moisture taken-up or given-up by the sample. In one embodiment the air used during the thermal fortification ranges from about 0 to about 100% relative humidity. In another embodiment the air ranges from about 50 to about 90% relative humidity. In another embodiment the air ranges from about 60 to about 85% relative humidity. In one embodiment the air is about 95% non-condensating. Greater than about 80% relative humidity results in aggressive moisture take-up. Different relative humidities will be appropriate for different types of product. As discussed, the humidity of the laboratory air can be controlled. In another embodiment the humidity of the analyzer is controlled. In such an embodiment humid air can be pumped to, or circulated through the closed analyzer to maintain a desired humidity. Likewise, the temperature of the air in the laboratory or within the analyzer can be controlled to adjust the rate of moisture taken-up by the sample.

In one embodiment the samples are loaded as previously described. Each sample is weighed to obtain an initial weight. Thereafter the sample is allowed to sit for a time to pick-up moisture until a specified moisture content has been reached. This is referred to as thermal fortification. The amount of time required to reach the desired moisture content will depend on a plurality of factors as discussed above. As will be discussed below, in one embodiment thermal fortification decreases the non-uniformity of the ramp profile and accounts for the inconsistencies of loading samples.

In one embodiment it is desirable that the sample increase its moisture content by about 1%. Those skilled in the art will understand that higher or lower increases may be suitable for different products. For example, some products may require moisture content increases of less than 1%, for example, about 0.3%, before thermal fortification has been achieved. In some embodiments, increasing the moisture content by more than about 10% can change how the product releases the moisture, which may be a negative consequence. This change can have an undesirable impact on the moisture reading. In one embodiment comprising a plurality of samples, the samples are allowed to pick-up moisture until each sample has been increased by at least 1%.

Figure 3:
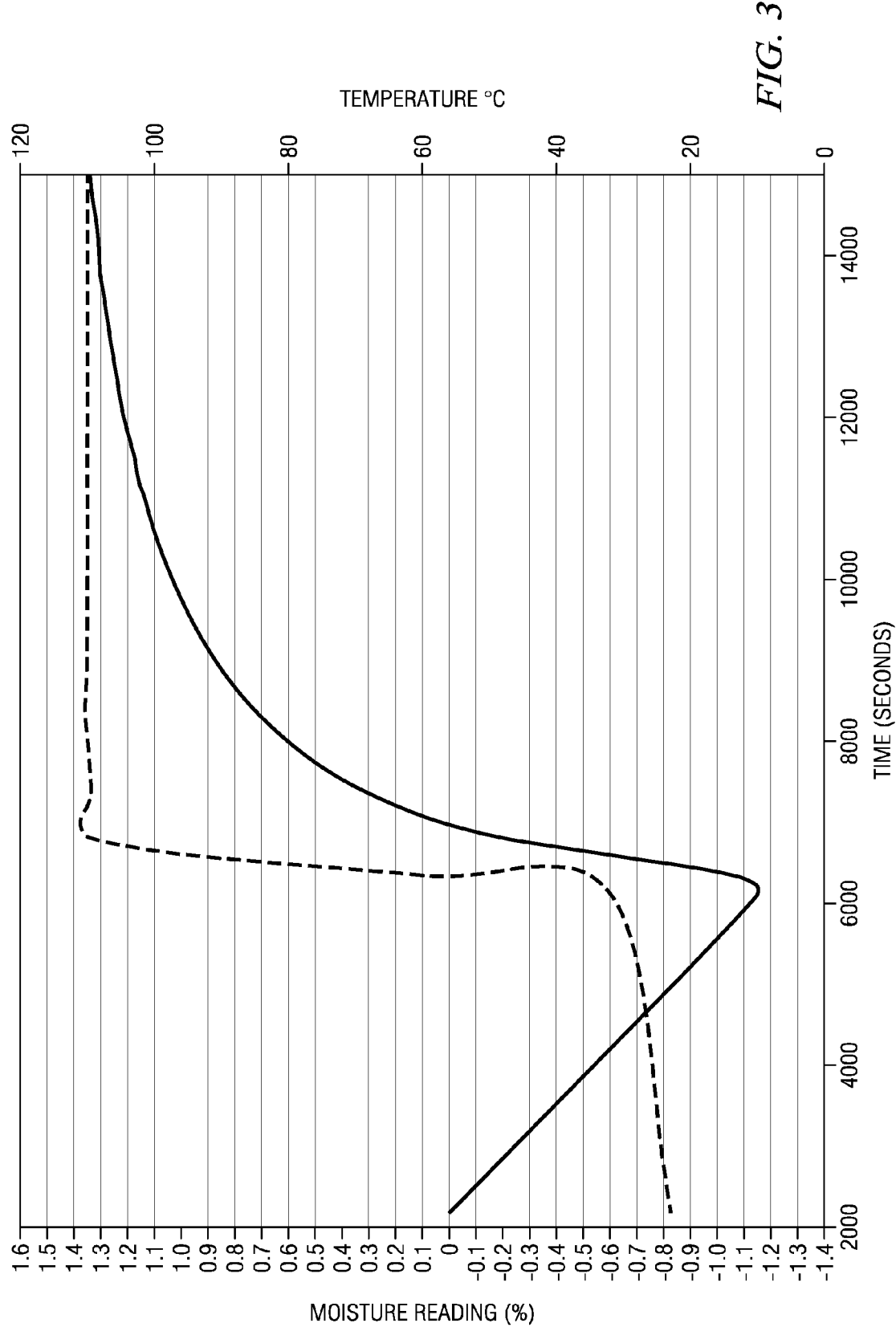
FIG. 3 is a temperature and moisture profile utilizing thermal fortification.

FIG. 3 shows a temperature and moisture profile for an analyzer using thermal fortification. The reference sample employed was a potato chip dough, and the sample was analyzed on a TGA 701. As depicted, the samples initially had a moisture reading of zero, meaning there had been no change in moisture content. They were allowed to sit for a time until the desired moisture is obtained. As depicted the set-point moisture reading is about 1.0%.

FIG. 3 also depicts the temperature profile of the analyzer. As depicted the ramp profile does not begin until the samples have obtained the desired moisture content. Put differently, the analyzer does not apply heat to obtain the set-point temperature until after a set-point moisture content has been obtained. It can be seen that once the sample obtains the moisture set-point, then the temperature of the analyzer increases. As the temperature increases, the sample begins to lose moisture. Thus, the moisture curve which previously had a negative slope now has a positive slope. At some point, the moisture curve passes the x-axis and a moisture reading of zero is obtained. At this point, the sample has returned to its initial weight before the fortifying. This means that the sample has lost the amount of moisture it had previously gained. This point is referred to as the fortified initial point.

The fortified initial point can be a data point or it can be calculated. As previously stated, in one embodiment samples are analyzed at scheduled intervals. As discussed, in one embodiment a given sample is analyzed every four minutes. Accordingly, in some embodiments a first data point will fall below the x-axis indicating a moisture gain while a second data point will fall above the x-axis indicating a moisture loss. This means that the fortified initial point occurred at some point between the first and second data point. Methods known in the art such as interpolation, regression, etc. can be used to determine the point in the time where the moisture reading is about zero. In such an embodiment the fortified initial point is calculated. The calculation can take place manually or can be calculated with software.

Referring to the temperature profile, as depicted, the temperature profile has been ramped by the time of the fortified initial point is reached. Put differently, the set-point temperature has been obtained prior to reaching the fortified initial point. This results in several benefits. As previously described, the temperature, the temperature profile, and the slope of the ramp-up have an affect on moisture. Because the set-point temperature is obtained, or obtained within an acceptable tolerance, before the fortified point is reached, the deviations due to non-uniform ramp profiles, temperature profiles, slopes, etc. is minimized or eliminated. As previously discussed these differences can be due in part to differences in controllers, process control equipment, temperature sensors, etc. across the various analyzers. The thermal fortification removes these variabilities and allows each sample to be treated in a uniform manner. Thus, in one embodiment by the time sample has again reached its initial weight at the initial fortified point the set-point temperature will have been obtained. Accordingly, each sample will be subject to the same temperature. As a result, each sample will have approximately the same heat supplied to the system as determined by the equation listed above.

As previously discussed, in some embodiments the analyzers will comprise a plurality of samples. In some embodiments only one sample can be weighed at a given time. As such, in one embodiment the first sample loaded will begin to take-up moisture while the other samples are being loaded. In such embodiments it is possible that the first sample will reach the moisture set-point faster than the later loaded samples. In one embodiment it is desirable to ensure that each sample reach the moisture set-point even if this means that the first sample may exceed the moisture set-point. This may also mean that each sample may have its own fortified initial point. Because the first sample may have exceeded the moisture set-point its fortified initial point may occur later in time compared to the later loaded samples. This is acceptable and only affects the time of test for that sample, which is discussed below.

In one embodiment the samples are analyzed until the final moisture set-point is obtained. In one embodiment the final moisture reading set-point is about 1.3. This means that the weight of the sample is decreased by about 1.3%. The point in time that the final moisture set-point is reached is referred to as the test finish point. As discussed with the fortified initial point, an analyzed data point may not fall on the test finish point. Specifically, a first data point may fall below the final moisture set-point and the second data point may fall above the final moisture set-point meaning the test finish point is located between the first and second data points. In such embodiments methods previously discussed can be used to calculated the test finish point. At the test finish time the final weight of the sample, and thus the moisture content of the sample is obtained or calculated.

The difference in time between the test finish point and the fortified initial point is referred to as the time of test. In one embodiment the time of test ranges from about 10 minutes to about 3 hours. In one embodiment the time of test is about 2 hours. As previously discussed, the amount of time from when the sample was first loaded into the analyzer until the test finish point is referred to as the total testing time. In one embodiment the total testing time ranges from about 20 minutes to about 9 hours. In one embodiment the total testing time is less than about 4 hours. The fortification method described above will increase uniformity and decrease variance.

In one embodiment, two or more samples are analyzed and the data is collected. In one embodiment as much as 10 or more samples are analyzed and the data collected. From this data an average curve can be created and the average time of test can be obtained. In one embodiment the time of test is the average time of test obtained from a plurality of samples. The obtained time of test can then be used in subsequent tests of that product to determine when the final moisture content is obtained. Specifically, the analyzer when analyzing that product will run for the time of test and the moisture reading at the end of the time of test will be utilized. In such an embodiment the test finish time occurs at a specified time after the initial fortified point. Thereafter a uniform test of time can be used in multiple runs. This results in a more uniform time of test which results in more uniform results. When the analyzer is referred to as running this means the analyzer is collecting data.

Figure 4:
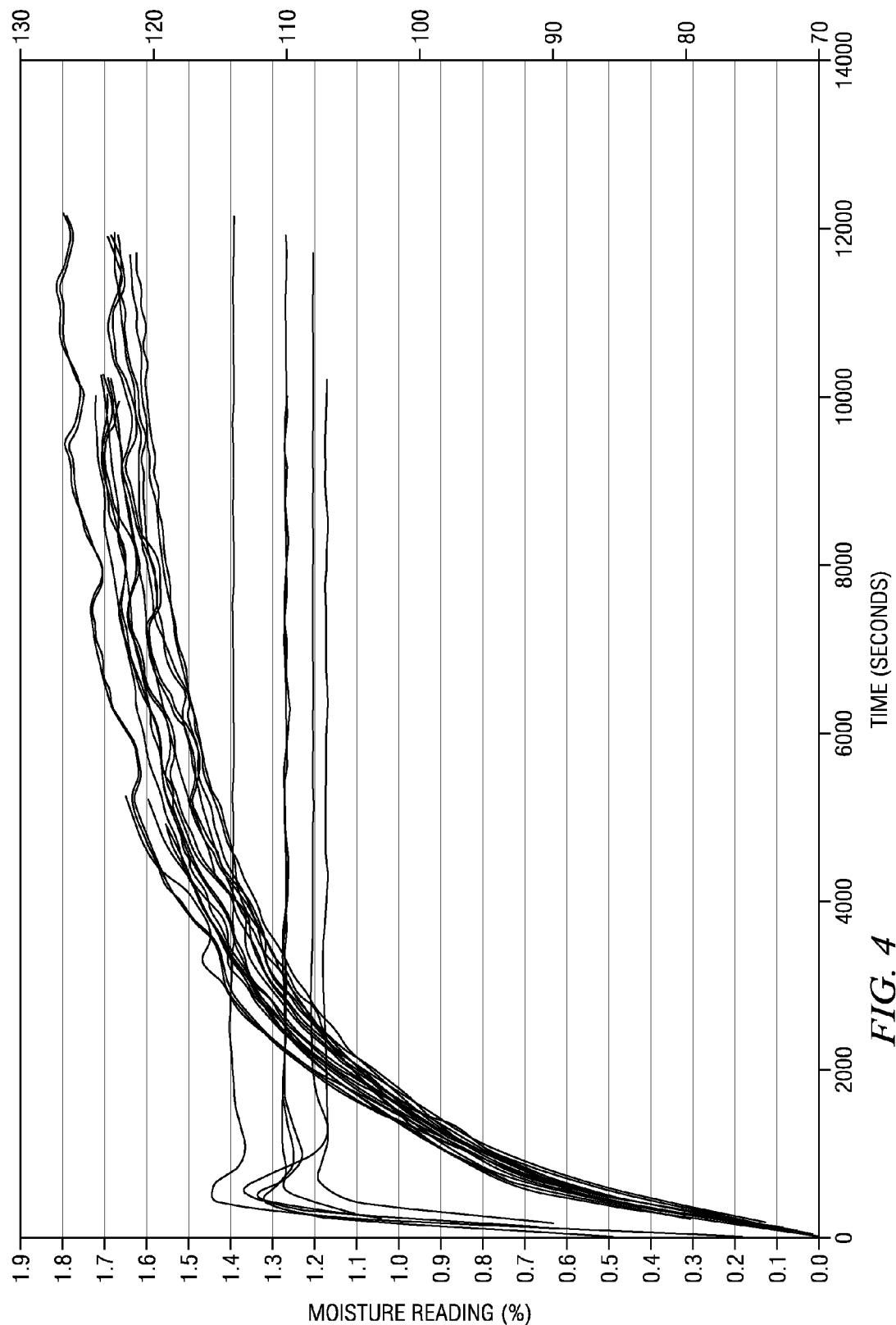
FIG. 4 is a temperature and moisture profile from a plurality of analyzers.

FIG. 4 is a temperature and moisture profile from a plurality of analyzers. The analyzers employed were TGA 701. Thermal fortification was not employed in the samples depicted in FIG. 4. As can be seen, compared to FIG. 1, FIG. 4 illustrates less variability in the ramp profile and moisture spread. This is due in part because all of the analyzers were located in a single location, thus, the boiling temperature remained constant across all analyzers. The analyzers were biased from a forced air oven reading. If the results from one of the analyzers deviated from the forced air oven reading by greater than 0.15% moisture the set-point temperature was adjusted 2° C. for each 0.5% deviation. This figure illustrates the variability in the ramp profile and the dehydration curves. This figure illustrates the total variability without using thermal fortification and without biasing each analyzer against a standard, which is discussed in detail below.

Figure 5:
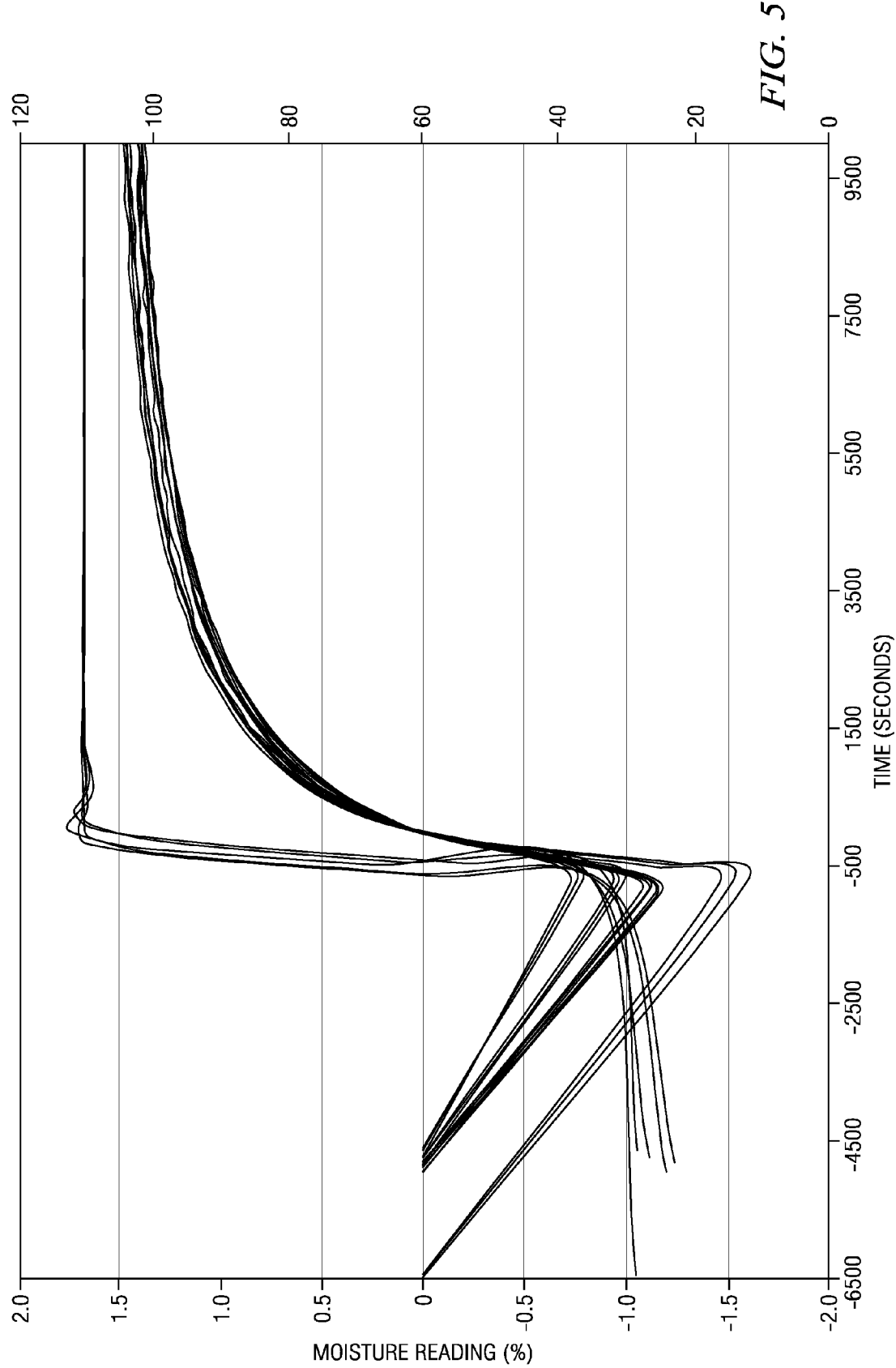
FIG. 5 is a temperature and moisture profile from the same analyzers of FIG. 4 but utilizing thermal fortification.

FIG. 5 is a temperature and moisture profile from the same analyzers of FIG. 4 but utilizing thermal fortification. The analyzers used in FIG. 5 were not biased but instead set to the same set-point temperature of 110° C. As can be seen the dehydration profiles in FIG. 5 still deviated slightly. This is due to the error of measuring the absolute temperature of the analyzer.

In FIG. 5 the samples were allowed to pick-up moisture for a specified amount of time. As can be seen, some samples were allowed to pick-up moisture for about 6500 seconds while other samples were allowed to pick-up moisture for about 4500 seconds. In the embodiment depicted, increasing the pick-up time had a minimal effect on the samples' profile. This is due in part to the set point temperature being achieved before the initial fortified point.

Figure 6:
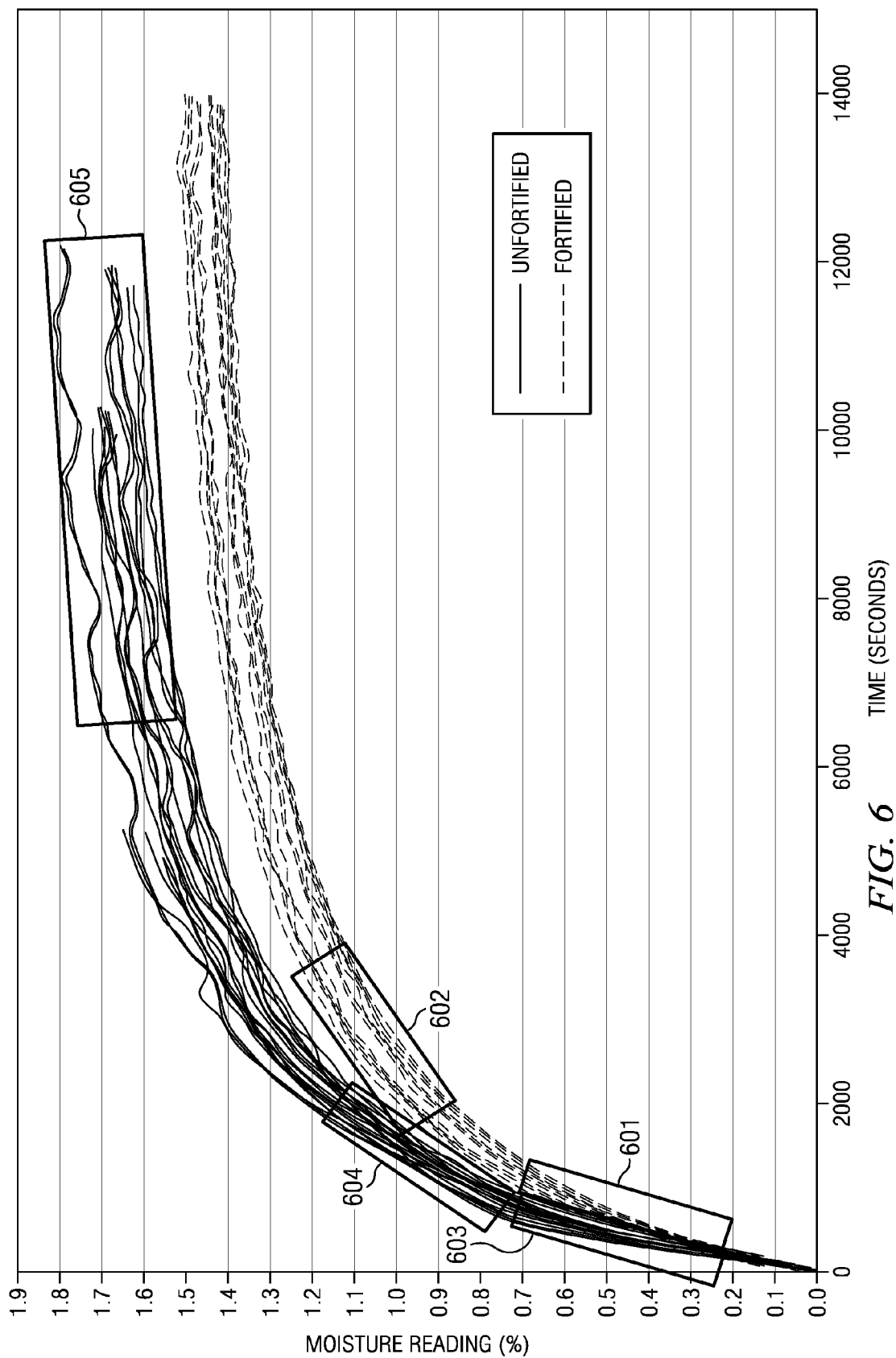
FIG. 6 illustrates the two dehydration curves from FIGS. 4 and 5.

FIG. 6 illustrates the two dehydration curves from FIGS. 4 and 5 on the same time axis. Put differently, the temperature and dehydration profiles of FIG. 5 have been time shifted so that the time zero is the approximate initial fortified point. As can be seen, the fortified samples (from FIG. 5) end at the same time. Put differently, they have a uniform test of time. Conversely, the un-fortified samples (from FIG. 4) end at dissimilar times.

As the curves begin it can be seen that the un-fortified samples achieve instant separation. This is shown in box 603. This is due in part because of dissimilar ramp profiles. After a short time the curves of the un-fortified groups become tighter due to different driving forces set by the temperature biasing. This is shown in box 604. Thereafter, the un-fortified samples again begin to diverge because of the large differences in dehydration driving force (difference in set-point temperature and boiling temperature) due to the compensation for the ramp profile variability. Put differently, because the ramp profiles were non-uniform the dehydration profiles diverge accordingly. This is illustrated in box 605. The fortified samples also have initial separation as shown in box 601. This is due to a difference in dehydration driving force due to error in the temperature measurement. Conversely, the curve separation for the fortified data samples remains similar as shown in box 602 because the dehydration driving force remains constant.

As can be seen, the dehydration curves of the fortified samples do not cross one another because the ramp profile variability has been dampened. As such the curves do not have to compensate for the ramp profile variability. More specifically, previously the systems were biased to accommodate the variability in ramp between systems. A high energy input during ramp for one system would likely mean a lower set point temperature to compensate for high moisture readings. Conversely, a low energy input ramping system would have a higher temperature set point to compensate for low moisture readings. Because ramp variability has been removed, the curves for the fortified samples do not cross one another. Conversely the dehydration curves of the un-fortified samples do cross one another. This is due in part to the differences in dehydration driving force used to compensate for ramp profile variability.

The method described can be used on a single analyzer or may be implemented in all analyzers for a given system. In some embodiments a system may comprise a plurality of analyzers. As an example, a system may comprise three dissimilar analyzers across the nation or across the world. As previously discussed, even if the analyzer is of the same brand with the same model, the results can vary greatly. As shown in FIG. 1, different analyzers yielded products which had a moisture reading difference of about 0.3%. As stated previously, this can result in an inconsistent product and inconsistent process control. As such, in one embodiment it is desirable to conform each analyzer so that the results are more uniform.

In one embodiment one analyzer is selected to be the "standard analyzer." The "standard analyzer" refers to the analyzer to which the satellite analyzers will be conformed and/or measured. The satellite analyzes refers to any analyzer in a system other than the standard analyzer. A satellite analyzer can be located across the country, in a different part of the world, or on the same shelf as the standard analyzer. In one embodiment each analyzer comprises a process variable which can be controlled. In one embodiment the process variable can be adjusted to obtain a desired set-point.

In one embodiment to conform the satellite analyzers to the standard analyzer the standard analyzer first analyzes a reference product set. A reference product set refers to an amount of similar product. In one embodiment a product set refers to product which is ground and homogenized to make the product as identical as possible. In one embodiment the reference product set comprises a sufficient amount of product to supply a plurality of analyzers. In one embodiment the product set is ground, placed inside a plastic sealable container such as a centrifuge tube. In one embodiment the container or set of containers is placed into a high barrier film bag. The bag is nitrogen flushed and sealed to prevent moisture pick-up or release. In one embodiment the seal comprises a material which acts as a moisture barrier. In one embodiment the sample is placed in a desiccating environment. Thus, in one embodiment the product set or sample is prepared by placing the sample in a container and sealing the container. Such a method will adequately maintain the approximate moisture content of each sample in the product set. Thereafter, at least one sample from the product set is loaded into the standard analyzer. The standard analyzer performs as previously described, and the sample is analyzed. The resulting curve is referred to as a standard analyzer profile. In one embodiment the standard analyzer profile comprises a temperature and dehydration profile. In one embodiment the analyzer utilizes the thermal fortification step previously described. Thereafter, at least one sample from the product set is then inserted into the satellite analyzer and the same method is performed. The resulting curve is referred to as the satellite analyzer profile and can include the same profiles as the standard analyzer profile. Thereafter the resulting curves from the standard analyzer and at least one satellite analyzer are compared. In one embodiment the resulting data is inserted into a computer program which biases the operation of the at least one satellite analyzer to match the profile produced by the standard analyzer. There are a variety of objective criteria which can be used to determine if the satellite analyzer sufficiently matches the profile produced by the standard analyzer. Those skilled in the art will understand that whether a satellite analyzer matches the standard analyzer will depend upon the acceptable margin of error. This can be quantified by using a coefficient of determination ($R^2$) or other statistical measurements. In one embodiment the average of four reference samples measured over two batches is compared to the standard analyzer, and if the difference in measured moisture content is less than about 1.0% then the satellite analyzer is considered to match the standard analyzer. In other embodiments the difference must be as low as 0.1%. In still other embodiments the difference must be less than about 0.05%. In one embodiment the biasing process is an iterative process.

In one embodiment the algorithm which biases at least one satellite analyzer utilizes Projections on Latent Structures (PLS) on dehydration curves and temperature set points to map out a latent space. In one embodiment the dehydration profile is an input and is used to determine the temperature offset for dehydration driving force relative to another system. By inputting the satellite system temperature set point, the biasing algorithm can report what temperature to set that system to so that if it were to run a reference sample, the resulting curve would best match a curve generated by a reference sample on the standard system. In one embodiment the standard system performs the biasing.

In one embodiment the underlying assumption is that while the absolute temperature of the analyzer is not being accurately measured by the temperature sensor, it is assumed that the relative temperature changes can be monitored accurately by the various temperature sensors. Put differently, it is assumed that while the actual absolute temperature of the analyzer is not measured correctly by the temperature sensor, the sensors are capable of detecting relative temperature change. As an example, if the temperature sensor provides a temperature reading of 105° C. but it is actually operating at 110° C., as measured by a separate temperature sensor, it is assumed that if the analyzer is adjusted to operate at 115° C. the temperature sensor will have a reading of 110° C. As previously discussed, the temperature difference between the set-point temperature and the boiling temperature is the driving force behind the heat transfer in the analyzer. As such, even if the actual set-point temperature is not known, so long as the relative temperature can be known and controlled, then the analyzer can be biased. Again even if the absolute operating temperature is unknown so long as the operating temperature can be adjusted and controlled then the analyzer can be biased. In this regard, the set point temperature variance issue is minimized as the set point is controlled even if the temperature sensor is reporting an incorrect operating temperature. Accordingly, at least one satellite analyzer is biased to duplicate the standard analyzer.

Such biasing and system operation allows direct comparison of results between analyzers, that under standard operating methods, would generate a significant systematic bias. Those skilled in the art will understand the multitude of benefits that flow from this direct comparison which include the ability to better control product attributes, better comparison of products from different plants, etc. As discussed, in one embodiment all analyzers will be controlling to the same moisture content at all sites that have been properly biased with this method. The result will significantly shrink the range of moisture content produced in all systems. As those skilled in the art will understand, moisture content is an important product attribute that must be controlled in consumer packed goods. Thus, this method allows for better control over moisture content which has many benefits.

In one embodiment after a satellite analyzer has been biased it can be used to create a gold standard curve and moisture reading for a specific product. The standard analyzer can also be used to create a gold standard. In one embodiment, a statistically significant number of samples are analyzed and the curves generated are averaged to create a gold standard. The gold standard shows the expected dehydration profile for reference product. When all other systems are biased to the standard analyzer, they should produce this curve on average when making the correct product.

In one embodiment wherein the satellite analyzer is located in a plant, the gold standard is created from hot product gathered at the plant. The standard system may be centrally located at a headquarters or lab where obtaining hot product is not possible. In one embodiment, the product samples used to create the gold standard is certified under standard protocol and hot samples from the production line are obtained and analyzed on the newly biased plant system. In one embodiment product produced, harvested, collected, or otherwise obtained is inserted into the analyzer and analyzed. In one embodiment product obtained from a manufacturing line is inserted into the analyzer.

In one embodiment the gold standard further dictates time of test required to reach the desired moisture reading if the system is being retrofitted to report a certain moisture specification. For example, if the gold standard notes that the time of test is 2 hours then subsequent samples are analyzed with a set-point temperature determined by the PLS biasing algorithm and run for a time of test of 2 hours beyond the point where the sample returns to its original weight after being allowed to gain moisture from the environment. In such an embodiment rather than operating until a moisture content is achieved the tests are run with a time of test of 2 hours. Thus, all tests utilizing that specific gold standard are uniform in length. In other embodiments, an arbitrary time of test may be chosen and the resulting moisture reading is the determined specification for that product. It should be noted that in some embodiments the elevation and system degradation of the satellite systems may result in a different test of time than that predicted by the gold standard.

Figure 7:
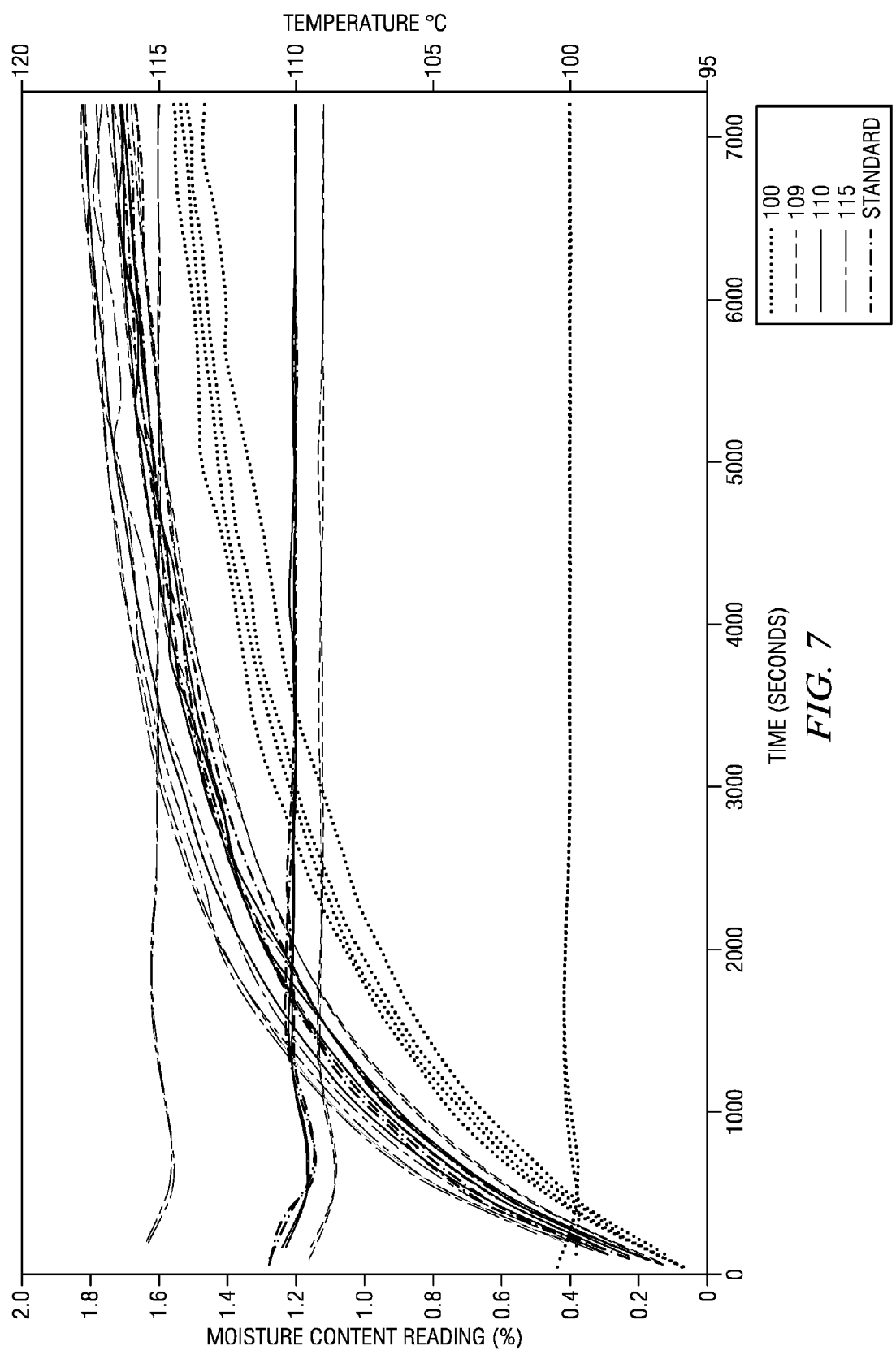
FIG. 7 illustrates the temperature and moisture profiles utilizing thermal fortification and biasing.

FIG. 7 illustrates the temperature and dehydration profile of a biased system. The model demonstrated in FIG. 7 was created by collecting data and curves from the standard analyzer across a variety of temperatures. The model was then used to predict temperature set points for the satellite analyzers.

The curves labeled "STANDARD" represent the standard analyzer profiles run with a set-point temperature of 110° C. The curves labeled "STANDARD" are the curves that the model is trying to replicate on the other satellite analyzers. The curves labeled 115 represent a satellite analyzer analyzing product from the same product set run with a set-point temperature of 115° C. The curves labeled 100 represent the same satellite analyzer as the curves labeled 115 analyzing product from the same product set but run with a set-point temperature of 100° C. The resulting curves labeled 115 were inputted into the model to obtain a predicted set-point for the satellite analyzer that would result in the satellite analyzer matching the standard analyzer. Using the curves labeled 115, and their initial set point of 115° C., the model yielded a set-point temperature of 110.1. Using the curves labeled 100, and their initial set point of 100° C., the model yielded a set-point temperature of 109.4° C. Thus, using different curves, the model predicted a substantially similar set-point temperature for the analyzer. The samples were analyzed on a TGA 701 as previously discussed. This model did not allow for adjustments of a fraction of a degree. Put differently, the set-point temperature can only be set to the nearest degree. Consequently, a validation trial was conducted at both 109° C., as predicted from the curves labeled 100, and at 110° C., as predicted from the curves labeled 115. The curves labeled 109 illustrate the satellite analyzer run with a set point of 109° C. whereas the curves labeled 110 illustrate the satellite analyzer run with a set point of 110° C.

The average final moisture content from the curves labeled "standard" was 1.68%. The average final moisture content from the curves labeled 100 was 1.51%, and the average final moisture content of the curves labeled 115 was 1.80%. After using the model, the average final moisture content of the curves labeled 109 was 1.70% whereas the average final moisture content of the curves labeled 110 was 1.74%. However, the final moisture content of the curves labeled 110 was calculated using an outlier which skewed the results. Those skilled in the art will understand that the effect of such outliers can be handled via statistical means. Further, those skilled in the art will understand that increasing the number of trials to obtain a more accurate mean will result in a more accurate model.

As those skilled in the art will understand, the analyzers can be used for a variety of purposes. In one embodiment the analyzers are used to calibrate process sensors. A process sensor includes any sensor that measures and/or controls any process variable on a process. As discussed, a process variable refers to any process condition which can be measured or controlled and includes, but is not limited to, moisture content, temperature, pressure, frying time, etc. A process variable also includes product attributes previously discussed including staleness, acrylamide concentration, etc. As discussed, product attributes are often controlled by controlling process variables.

In one embodiment the process sensors comprises an on-line sensor. In one embodiment the on-line sensors are used to control the operation of the process. However, periodically samples are tested with an analyzer to calibrate the on-line sensors. The method discussed herein allows the analyzer to become more precise, accurate and more uniform across all analyzers in a system. This accuracy and uniformity is then passed to other processing equipment, such as the on-line sensors, through calibration and the like. In such embodiments, the data from the analyzer is transmitted to the process sensor. The data can be transmitted via hardwire, wireless, or other method known in the art. It should be understood that the data can be transmitted directly to the process sensor, or it can be transmitted to a controller which controls or monitors the process sensor. In one embodiment, the process sensor measures at least one process variable. The measured process variable from the process sensor is then compared to the data received from the analyzer, and the process sensor is calibrated using the data received.

In another embodiment, the data collected from the analyzer is sent to controller, whereby the controller utilizes the data to determine if process variables should be adjusted. As an example, the controller may determine that the on-line process sensor needs calibrated. It may also determine, for example, that frying time needs to be increased.

As previously discussed, moisture content has an affect on many product attributes including staleness, number of defects, level of scorching, acrylamide formation, product hardness, etc. As discussed, these and other attributes can be better controlled by better controlling the moisture content. One such example is acrylamide. Those skilled in the art understand that acrylamide increases exponentially as the moisture content is reduced. Thus, if the moisture content is increased, the level of acrylamide can be significantly reduced. In one embodiment involving fried potato chips, it has been determined that increasing the average moisture content from 1.1 to 1.3 resulted in a 25% reduction in acrylamide formation.

In an embodiment involving fried potato chips, a variance of about 0.4% moisture content resulted in about 100-150 ppb additional acrylamide in some lower moisture product. Put differently, a 0.4% variance resulted in some product having less moisture which resulted in additional acrylamide. As noted in FIG. 1, a 0.4% variance in moisture content had previously been common as the analyzers often had undesirable variability for the reasons discussed herein. Further, because the level of acrylamide increases exponentially as the moisture content is decreased, a product which has 0.4% less moisture content than desirable has more acrylamide compared to the product with the desired moisture content. As such, decreasing this variance allows a significant reduction in acrylamide formation.

In embodiments wherein the variance of moisture content is reduced to about 0.05% then the amount of additional acrylamide is from about 0 to about 25 ppb. In embodiments wherein the mean acrylamide concentration is about 300 ppb this method resulted in a 30% increase with the 0.4% moisture content variance to a reduction of less than a 10% increase with the 0.05% moisture content variance in moisture content. As will be understood by those skilled in the art, methods can be applied which will further decrease the variance below 0.05%. For example, a wider selection of samples will yield a more accurate mean, which in turn will develop a more accurate model. Further, larger samples allow for statistical methods which can locate and eliminate undesirable outliers which can also result in a more accurate model. Those skilled in the art will understand the tools and methods to obtain a more accurate model.

As discussed above, the data obtained from the analyzer can be fed to the manufacturing line which can adjust the process control based on the obtained data. Accordingly, having decreased variance in the moisture content translates to decreased variance in the process control. As described above, decreasing the variance in the analyzer allows tighter and more consistent control over the process control, which can then be used to control, and reduce, the formation of acrylamide, as an example.

While the invention has been particularly shown and described with reference to a preferred embodiment, it will be understood by those skilled in the art that various changes in form and detail may be made therein without departing from the spirit and scope of the invention.

Additional Description

The following clauses are offered as further description of the disclosed invention.

1. A method for analyzing moisture content in an analyzer, said analyzer comprising:
   at least one balance;
   said method comprising:
   a) introducing at least one sample into said analyzer;
   b) obtaining an initial weight of said at least one sample with said balance;
   c) fortifying said at least one sample to obtain a desired moisture content;
   d) increasing the temperature of said analyzer;
   e) obtaining an initial fortified point, wherein said at least one sample has returned to said initial weight at said initial fortified point;
   f) obtaining the moisture content of said at least one sample at a test finish time.
2. The method according to any preceding clause, wherein said fortifying step comprises allowing said at least one sample to pick-up moisture.
3. The method according to clause 2 wherein said desired moisture reading comprises increasing the moisture content of said at least one sample by 1%.
4. The method according to any preceding clause, wherein said introducing comprises introducing at least two samples.
5. The method according to any preceding clause, wherein said introducing comprises introducing into a thermogravimetric analyzer.
6. The method according to any preceding clause, wherein said increasing of step d) comprises increasing to a set-point temperature.
7. The method according to clause 6, wherein said set-point temperature is obtained prior to said obtaining of step c).
8. The method according to any preceding clause, wherein said increasing of step d) takes place after said at least one sample has reached said desired moisture reading in step c).
9. The method according to any preceding clause, wherein said test finish time is a point in time wherein said at least one sample reaches a desired moisture reading.
10. The method according to any preceding clause, wherein said test finish time occurs at a specified time after said initial fortified point.
11. The method according to clause 10, wherein said specified time after said initial fortified point is uniform across multiple runs.
12. The method according to clause 10, wherein said specified time after said initial fortified point comprises a test of time.
13. The method according to clause 12, wherein said test of time is the difference in time between said initial fortified point and said finish time.
14. The method according to clause 13, wherein said test of time comprises an average of a plurality of test of times observed from at least two samples.
15. The method according to clause 10, further comprising:
    g) repeat steps a-f, wherein said specified time after said initial fortified point is about the same in step f) and step g).

16. The method according to any preceding clause, wherein said obtaining of step e) comprises calculating an initial fortified point.
17. The method according to clause 16, wherein said calculating comprises interpolating between data points.
18. The method according to any preceding clause, wherein said obtaining of step f) comprises calculating the moisture content.
19. The method according to clause 18, wherein said calculating comprises extrapolating between data points.
20. The method according to any preceding clause, wherein said obtaining of step b) comprises weighing said at least one sample with said balance.
21. The method according to any preceding clause, wherein said fortifying of step c) comprises fortifying in a humidity controlled environment.
22. The method according to any preceding clause, further comprising:
    g) transmitting said moisture content to a process sensor.
23. The method according to clause 22, further comprising:
    h) analyzing at least one process variable with said process sensor.
24. The method according to clause 23, further comprising:
    i) calibrating said process sensor.
25. The method according to clause 22, further comprising:
    i) adjusting at least one process variable.
26. A method for biasing an analyzer in system, said system comprising:
    at least two analyzers, wherein said at least two analyzers comprises a standard analyzer and a first satellite analyzer, and wherein each analyzer comprises at least one process variable;
    said method comprising:
    a) obtaining a product set comprising a plurality of samples, wherein said plurality of samples comprises a first sample and a second sample;
    b) analyzing said first sample in said standard analyzer to obtain a standard analyzer profile;
    c) analyzing said second sample in said first satellite analyzer to obtain a first satellite analyzer profile;
    d) comparing said standard analyzer profile with said first satellite analyzer profile;
    e) biasing said first satellite analyzer to said standard analyzer.
27. The method according to clause 26, wherein said biasing comprises utilizing projections on latent structures on set-point temperature and dehydration curves.
28. The method according to clause 27, wherein said set-point temperature is an input and dehydration profile is an output.
29. The method according to clauses 26-28, further comprising:
    f) analyzing a plurality of samples on said first satellite analyzer to obtain a gold standard curve.
30. The method according to clause 29, further comprising:
    g) obtaining a test of time from said gold standard curve.
31. The method according to clause 30, further comprising:
    h) analyzing at least one sample by running said first satellite analyzer for a test of time.
32. The method according to clauses 26-31, wherein said analyzing of step b) comprises thermal fortification.
33. The method according to clauses 26-32, wherein said standard analyzer profile comprises a dehydration profile.
34. The method according to clauses 26-33, wherein said standard analyzer profile comprises a temperature profile.
35. The method according to clause 27, wherein said standard analyzer is a thermogravimetric analyzer.
36. The method according to clauses 26-35, wherein said analyzing of step b) comprises obtaining a moisture content.
37. The method according to clauses 26-36, wherein said obtaining of step a) comprises sealing said plurality of samples.
38. The method according to clauses 26-37, wherein said obtaining of step a) comprises nitrogen flushing and sealing said plurality of samples.
39. The method according to clauses 26-38, wherein said biasing of step e) results in decreased moisture content variances.
40. The method according to clauses 26-39, wherein said biasing of step e) results in decreasing the level of acrylamide formation.
41. The method according to clauses 26-40, wherein said biasing step comprises biasing said first analyzer to yield a moisture content within 0.05% of a moisture content yielded by said standard analyzer.

What is claimed is:
1. A method for biasing an analyzer in system, said system comprising:
    at least two analyzers, wherein said at least two analyzers comprises a standard analyzer and a first satellite analyzer, and wherein each analyzer comprises a device which can determine a moisture content in a hygroscopic sample and wherein the first satellite analyzer is an analyzer in a system other than that of the standard analyzer;
    said method comprising:
    a) obtaining a product set comprising a plurality of hygroscopic samples, wherein said plurality of hygroscopic samples comprises a first hygroscopic sample and a second hygroscopic sample;
    b) analyzing said first hygroscopic sample in said standard analyzer to obtain a standard analyzer profile;
    c) analyzing said second hygroscopic sample in said first satellite analyzer to obtain a first satellite analyzer profile;
    d) comparing said standard analyzer profile with said first satellite analyzer profile;
    e) biasing said first satellite analyzer to said standard analyzer;
    wherein said biasing comprises utilizing projections on latent structures on set-point temperature and dehydration curves, wherein the set-point temperature for each analyzer is adjusted to ensure dehydration driving force remains substantially constant.
2. The method of claim 1 wherein said set-point temperature is an input and dehydration profile is an output.
3. The method of claim 1 further comprising:
    f) analyzing a plurality of samples on said first satellite analyzer to obtain a gold standard curve.
4. The method of claim 3 wherein said gold standard curve dictates a time to reach a desired moisture reading in a sample.
5. The method of claim 3 wherein said gold standard curve dictates an expected dehydration profile in a sample.
6. The method of claim 1 wherein said analyzing of step b) comprises thermal fortification, wherein said thermal fortification allows for the plurality of hygroscopic samples to pick-up moisture for a specified amount of time to reach a moisture set-point.
7. The method of claim 6 wherein the thermal fortification comprises allowing the plurality of samples to pick-up moisture until a moisture content of each sample has been increased by at least 1%.

8. The method of claim 6 comprising the step of controlling humidity of the analyzer or air surrounding the analyzer from 0 to 100% relative humidity.

9. The method of claim 1 wherein said standard analyzer profile comprises a dehydration profile.

10. The method of claim 1 wherein said standard analyzer profile comprises a temperature profile.

11. The method of claim 1 wherein said standard analyzer is a thermogravimetric analyzer.

12. The method of claim 1 wherein said analyzing of step b) comprises obtaining a moisture content.

13. The method of claim 1 wherein said obtaining of step a) comprises sealing said plurality of samples with a seal that comprises a material that acts as a moisture barrier.

14. The method of claim 1 wherein said obtaining of step a) comprises nitrogen flushing and sealing said plurality of samples.

15. The method of claim 1 wherein said biasing step comprises biasing said first analyzer to decrease measured moisture content variances in said samples.

16. The method of claim 1 wherein said biasing step comprises biasing said first analyzer to decrease the level of acrylamide formation in a product with less moisture than desirable.

17. The method of claim 1 wherein said biasing step comprises biasing said first analyzer to yield a measured moisture content in said samples within 0.05% of a measured moisture content yielded by said standard analyzer.

18. The method of claim 1 wherein the plurality of samples of the product set supplies a plurality of analyzers.

19. The method of claim 1 wherein the product set comprises product which is ground.

\* \* \* \* \*